United States Patent [19]

Myers, Jr.

[11] 4,225,736
[45] Sep. 30, 1980

[54] CODIMER OF NORBORNADIENE AND CYCLOHEXADIENE

[75] Inventor: Harry K. Myers, Jr., Aston, Pa.

[73] Assignee: Sun Oil Company of Pennsylvania, Philadelphia, Pa.

[21] Appl. No.: 30,967

[22] Filed: Apr. 17, 1979

Related U.S. Application Data

[60] Division of Ser. No. 933,231, Aug. 14, 1978, which is a continuation of Ser. No. 818,489, Jul. 25, 1977, abandoned.

[51] Int. Cl.$^2$ .............................................. C07C 13/28
[52] U.S. Cl. ................................. 585/360; 585/362; 149/109.4; 60/208
[58] Field of Search .............................. 585/362, 360; 149/109.4

[56] References Cited

U.S. PATENT DOCUMENTS

| | | | |
|---|---|---|---|
| 2,831,037 | 4/1958 | Schmerling | 585/362 |
| 3,258,502 | 6/1966 | Cannell | 585/362 |
| 3,329,732 | 7/1967 | Bastiau | 585/362 |
| 4,094,916 | 6/1978 | Thomas | 585/362 |
| 4,094,917 | 6/1978 | Thomas | 585/362 |

OTHER PUBLICATIONS

Greco et al., J. Org. Chem., 35, No. 1, 271, 1970.
Carbonaro et al., J. Org. Chem., 36, No. 10, 1443, 1971.

*Primary Examiner*—Veronica O'Keefe
*Attorney, Agent, or Firm*—J. Edward Hess; Donald R. Johnson; Anthony Potts, Jr.

[57] ABSTRACT

Novel codimer (I) of norbornadiene and 1,3-cyclohexadiene and its hydrogenated derivative (II), having the following structures:

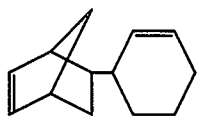 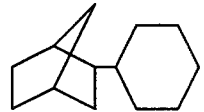

(I)　　　　　(II)

and processes for preparing both are disclosed. Product (II) can be used as a high energy fuel. Process for codimer I involves use of three component homogeneous catalytic system of cobaltic or cobaltous acetylacetonate, 1,2-bisdiphenylphosphino ethane and one of three alkyl aluminum chlorides.

10 Claims, No Drawings

CODIMER OF NORBORNADIENE AND CYCLOHEXADIENE

CROSS REFERENCE TO RELATED APPLICATION

This is a division of application Ser. No. 933,231, filed Aug. 14, 1978, which is a continuation of application Ser. No. 818,489, filed July 25, 1977 abandoned.

BACKGROUND OF THE INVENTION

The invention herein described was made in the course of or under a contract thereunder with the United States Air Force Systems Command.

The invention relates to the catalytic codimerization of norbornadiene and 1,3-cyclohexadiene. Particularly the invention relates to the preparation of an olefinic codimer of norbornadiene and 1,3-cyclohexadiene using a specified catalyst system. Hydrogenation of the olefinic codimer yields a saturated codimer having utility as a high energy fuel or a diluent for such fuels. The cyclohexadiene is referred to hereinafter as CHD.

High energy fuel, which is often referred to as a high density fuel, can be used in either jet or rocket propulsion. Jet propulsion includes a jet engine which can be used for a missile plane and others and includes the three basic types, i.e., ramjet, turbo-jet and pulse jet. The term rocket generally refers to a device containing its own oxygen or oxidizing agent.

Norbornadiene is also known as bicyclo-(2.2.1) heptadiene-2,5. A method of preparation is disclosed in U.S. Pat. No. 2,875,256 issued Feb. 24, 1959. Hereinafter, norbornadiene is referred to as NBD. The latter can be represented by either one of the following structural formulas:

NBD can be easily dimerized to an exo-exo hexacyclic dimer. Thus one problem in reacting NBD with another hydrocarbon reactant is to minimize the formation of the foregoing dimer while encouraging the formation of the desired codimer.

SUMMARY OF THE INVENTION

NBD and CHD are codimerized to a codimer having the following structure:

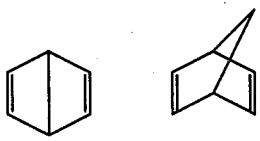

I

Hydrogenation of codimer I yields product II having the following structure:

II

Product II can be used as a high density missile fuel.

The codimerization to codimer I involves the use of a catalytic amount of a three-component homogeneous catalytic system consisting of cobaltic or cobaltous acetylacetonate, 1,2-bisdiphenylphosphino ethane and one of three alkyl aluminum chlorides.

DESCRIPTION

Cobaltic acetylacetonate (Co(C$_5$H$_7$O$_2$)$_3$) is referred to hereinafter as CoA$_3$ whereas the cobaltous form (Co(C$_5$H$_7$O$_2$)$_2$) is referred to as CoA$_2$; collectively the two are referred to as CoA. The 1,2-bisdiphenylphosphino ethane is referred to as DIPHOS while the alkyl aluminum chloride is referred to as AAC.

The catalytic codimerization of NBD and CHD via present invention can be represented by the following formula reaction:

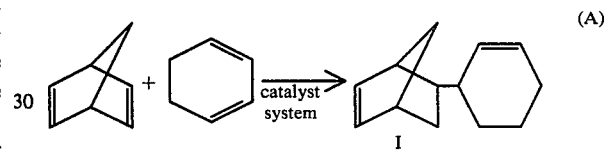

(A)

As shown NBD and CHD are contacted in the presence of a catalytic amount of the catalyst system defined herein. Coproducts may also be formed.

Codimer I upon hydrogenation forms product II. The hydrogenation of olefinic codimer I can be represented by the following formula reaction:

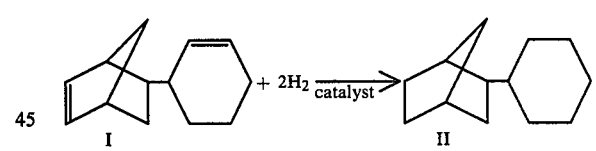

A hydrogenation catalyst such as PtO$_2$ can be used.

The NBD used can contain a nominal amount of similar hydrocarbons, however, which if present should not be of a type which could adversely effect the reaction. If the NBD used contains undesirable hydrocarbons, they can be removed by known means. The foregoing also applies to the CHD used. Thus the hydrocarbons used in the invention can consist essentially of NBD and CHD.

In the codimerization of NBD and CHD one mole of each reacts with the other to form one mole of the NBD-CHD codimer II. However, if the NBD to CHD mole ratio is too large homodimerization can occur with an adverse effect on codimer yields. On the other hand, if the NBD to CHD mole ratio is too low then the yield per pass can be too low and hence uneconomical. Within the aforementioned range a preferred NBD to CHD mole ratio is in the range between from about 0.01 to about 10 about 0.1 to about 5 preferred.

The catalytic system favoring the aforementioned codimerization reaction A contains three components.

All three components of the catalyst system are commercially available and methods for their preparation are reported in the literature. The three are $CoA_3$ or $CoA_2$, DIPHOS and AAC. The AAC can be selected from the group consisting of diethylaluminum chloride, ethyl aluminum dichloride and ethyl aluminum sesquichloride. The latter three are referred hereinafter to as DEAC, EADC and EASC, respectively. The amount of any component present is a catalytic amount so that a suitable conversion to codimer II occurs and the selectivity as to it is sufficient. Material, which during the codimerization reaction could adversely affect the catalyst system, should not be present. For example, the presence of hydroxylic compounds such as water, alcohol or oxygen from air could deactivate the catalyst system.

The amount of the CoA present should be catalytically sufficient to obtain the desired product. Generally the NBD to CoA mole ratio can range between from about 10 to about 2000 with a preferred range between from about 20 to about 1000.

The second component of the catalyst system is DIPHOS which has the following formula: $[(C_6H_5)_2PCH_2]_2$. The amount of this second component of the catalyst system should be catalytically sufficient to obtain the desired product. Generally the DIPHOS to CoA mole ratio can range between from about 0.1 to about 5 with a preferred range between from about 1 to about 4.

DEAC, EADC or EASC is the third component of the catalyst system with DEAC preferred. The amount of the third component can vary substantially but generally it relates to the amount of CoA used. An effective DEAC, EADC or EASC to CoA mole ratio can be between from about 0.5 to about 100 with from about 1 to about 50 preferred and from about 3 to about 20 more preferred. Generally, when DEAC, EADC or EASC is used it is advantageous to conduct the reaction under substantially anhydrous conditions and under an inert gas blanket. Excess DEAC, EADC or EASC also serves as a scavenger.

Selectivity refers to the amount, mole or weight, of a particular compound formed divided by the amount of all compounds formed. From a commercial standpoint the economics of an overall process determines the optimal levels for both the selectivity and yield.

The reaction time required for an economically satisfactory selectivity and/or yield depends on a number of factors, such as catalyst to feed ratio, as well as operating conditions. Also the economics depend on capital investment versus conversion per pass and the like. The catalyst to feed ratios are discussed herein while typical conditions are provided by the Example.

A solvent can be used in the codimerization reaction. The solvent can be inert or it can be the NBD itself. Since the reaction is mildly exothermic the solvent can serve as a heat sink. It can also assist in solubilizing the reaction components, that is the feed and the components of the catalyst, and thereby provide for a homogeneous reaction medium. Some solvent can be added to the system as a carrier for one or more of the catalyst components. For example, DEAC is often maintained in an inert solvent such as toluene rather than NBD itself. Furthermore, the solvent should not adversely react with the feed, products or catalyst, therefore, if it is not NBD, it should be inert. Also, presence of the solvent can facilitate the handling of the reaction mixture. Classes of suitable inert solvents include aromatic hydrocarbons, cycloparaffins, cycloolefins, ethers, halogenated aromatics, halogenated paraffins and halogenated cycloparaffins. Specific examples include benzene, toluene, xylenes, cyclohexane, cyclopentadiene, diethylether, chlorobenzene, bromobenzene, chlorinated cyclohexane and the like. As to the amount of solvent used, excessive amounts decrease the reaction rate, and thus adversely affect the economics for a commercial operation.

The codimerization of NBD and CHD with the three-component catalyst system can occur at ambient temperature. Thus the temperature of the homogeneous feed catalyst system mixture need not be raised to initiate reaction A. However, if the mixture is at an extremely low temperature, then heating of the cooled mixture could be necessary. Furthermore, once reaction A is underway, some heat is generated and the temperature of the mixture increases. If the temperature increases too much then some cooling would be required. Generally however, the codimerization of NBD and CHD with a reasonable amount of the three-component catalyst system is not characterized by an extremely rapid exotherm.

Selective codimerization of the NBD and CHD most efficiently occurs in a liquid phase and therefore it is not desirable to have the reaction temperature largely exceed the boiling points of the NBD and/or any solvent. Conversely, if the temperature is too low the reaction rate could be too low to be economically feasible. An operable temperature range is between from about 20° C. to about 100° C. with about 25° C. to about 85° C. a preferred range. The operating pressure can vary substantially, however, it can range from about atmospheric up to about 2000 psi with about 1000 psi a preferred upper value. Process economics favor lower operating pressure, however, a moderately elevated reaction pressure may be desirable to keep the NBD in solution.

To further illustrate the invention, the following examples and comparative effort are provided.

EXAMPLES

The codimerization of the CHD and NBD was carried out in the following manner. In a Fisher-Porter glass pressure vessel were mixed 0.356 grams of $CoA_3$, 0.597 grams of DIPHOS, 15 milliliters of toluene, 5 milliliters of NBD and one milliliter of CHD all at room temperature. The resulting mixture was cooled to −20° C. Into a second glass pressure vessel were added 30 milliliters of NBD and 10 milliliters of CHD. This second mixture was deaerated at room temperature.

Then 15 milliliters of a one molar solution of DEAC in toluene were added to the first pressure vessel during which the temperature of the resulting mixture rose from −20° C. to 40° C. Then the contents of the second vessel were slowly pumped into the first vessel and an exothermic reaction resulted. After 20 minutes the temperature of the exothermic mixture reached 50° C. where it was maintained for 5 minutes by external cooling. Then the temperature was allowed to rise to about 61° C. where it was maintained throughout the remainder of the reaction.

The reaction mixture was sampled at 30 minutes, 86 minutes, 124 minutes and at 240 minutes. Each sample was immediately quenched with aqueous HCl and then analyzed. The remaining total reaction mixture was quenched with aqueous HCl after 300 minutes. Analytical results were obtained by vapor phase chromatographic analysis. The data indicated that the CHD gradually reacted for about 170 minutes after which the reaction appeared to cease.

The results of the foregoing analytical results are as shown in the accompanying Table.

TABLE

| Time, Min. | % Conversion of Monomer[a] | A<br>% Yield of Codimers[a] | B<br>% Yield of NBD-dimers[a] | Ratio of A/B |
|---|---|---|---|---|
| 30 | 11.6 | 5.1 | 6.4 | 0.8 |
| 86 | 17.7 | 7.2 | 10.2 | 0.7 |
| 124 | 24.0 | 9.8 | 14.1 | 0.7 |
| 170 | 26.4 | 12.1 | 15.5 | 0.8 |
| 240 | 25.0 | 10.5 | 14.2 | 0.75 |

[a]Weight of total NBD + CHD converted.

A product mixture, after quenching, was distilled. A cut of 9.6 grams boiling at 54°–59° C. at 0.2 mm Hg. was obtained and chromatographic analysis showed it to contain 53% codimer and 44% exo-exo hexacyclic NBD dimer. The foregoing cut had a melting point of −95° C. as determined by differential scanning calorimetering. The cut had a density of 1.0359 grams per milliliter and a net volumetric heat of combustion of 156,768 BTU/gal.

A portion of the cut was hydrogenated using $PtO_2$ at ambient temperature and a hydrogen pressure of about 80 psi. Other similar hydrogenation catalysts will work equally well. A sample of the hydrogenated material was analyzed as to its composition and structure.

Structure I and II were confirmed by infrared and NMR spectra and other such tests.

Analogous results will be obtained when $CoA_2$ is used in lieu of $CoA_3$ and/or when DEAC is replaced by either EADC or EASC.

In contrast to the foregoing, unsuccessful attempts were made to react NBD with CHD using other various catalysts. The catalyst systems used and the major products are as follows:

| CATALYST SYSTEM[a] | TEMP. °C. | MAJOR PRODUCT OF REACTION |
|---|---|---|
| $FeA_3$-DEAC-TPP | 80 | none |
| $FeA_3$-DEAC-DIPHOS | 80 | none |
| $Ni(CPD)_2$ | 60 | none |
| $Fe(CPD)_2$ | 60 | none |

[a]TPP = triphenylphosphine
CPD = cyclopentadiene

The foregoing were conducted in a similar fashion as to the first reported run however small amounts were used and the reaction mixture was quenched with isopropyl alcohol. Samples of the resultant material were analyzed via the same chromatography methods reported previously.

The invention claimed is:

1. Process for the catalytic codimerization of norbornadiene and 1,3-cyclohexadiene comprising:
   (a) contacting norbornadiene and 1,3-cyclohexadiene in the presence of a catalytic amount of a three-component homogeneous catalytic system consisting of cobaltic or cobaltous acetylacetonate, 1,2-bisdiphenylphosphino ethane and one of the following alkyl aluminum chlorides: diethylaluminum chloride, ethyl aluminum dichloride and ethyl aluminum sesquichloride;
   (b) having the contacting occurring at a temperature within the range from between about 20° C. to about 100° C.; and
   (c) continuing the contacting until the codimer of norbornadiene and 1,3-cyclohexadiene is prepared.

2. Process according to claim 1 wherein the bisdiphenylphosphino ethane to the acetylacetonate mole ratio is in the range between from about 0.1 to about 5.

3. Process according to claim 1 wherein the norbornadiene to the 1,3-cyclohexadiene mole ratio is in the range between from about 0.01 to about 10.

4. Process according to claim 1 wherein the alkyl aluminum chloride to the acetylacetonate mole ratio is in the range between from about 0.5 to about 100.

5. Process according to claim 1 wherein the norbornadiene to the acetylacetonate mole ratio is in the range between from about 10 to about 2000.

6. Process according to claim 5 wherein an inert solvent is present.

7. Process according to claim 6 wherein the inert solvent is selected from the group consisting of aromatic hydrocarbon, cycloparaffin, cycloolefin, ether, halogenated aromatic, halogentated paraffin and halogenated cycloparaffin.

8. Process according to claim 7 wherein the bisdiphenylphosphino ethane to the acetylacetonate mole ratio is in the range between from about 0.1 to about 5.

9. Process according to claim 8 wherein the alkyl aluminum chloride to the acetylacetonate mole ratio is in the range between from about 0.5 to about 100.

10. Process according to claim 9 wherein the norbornadiene to the 1,3-cyclohexadiene mole ratio is in the range between from about 0.01 to about 10.

* * * * *